United States Patent
Inoue et al.

(10) Patent No.: US 6,544,243 B1
(45) Date of Patent: Apr. 8, 2003

(54) DISPOSABLE DIAPER

(75) Inventors: Yasushi Inoue, Kagawa-ken (JP); Yasushi Sayama, Kagawa-ken (JP); Shunsuke Fujino, Ehime-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 1112 days.

(21) Appl. No.: 08/948,052

(22) Filed: Oct. 9, 1997

Related U.S. Application Data

(63) Continuation of application No. 08/632,828, filed on Apr. 16, 1996, now abandoned.

(30) Foreign Application Priority Data

Apr. 24, 1995 (JP) ................................. 7-098467

(51) Int. Cl.⁷ ........................ A61F 13/15; A61F 13/20
(52) U.S. Cl. ...................... 604/385.28; 604/385.26; 604/378
(58) Field of Search .............. 604/385.1–402, 604/385.28, 385.26, 378

(56) References Cited

U.S. PATENT DOCUMENTS

| | | | | |
|---|---|---|---|---|
| 3,860,003 A | * | 1/1975 | Buell | 604/385.2 |
| 4,795,454 A | * | 1/1989 | Dragoo | 604/385.2 |
| 5,246,432 A | * | 9/1993 | Suzuki et al. | 604/385.2 |

FOREIGN PATENT DOCUMENTS

| | | | | |
|---|---|---|---|---|
| JP | 3218751 | * | 9/1991 | 604/385.1 |
| JP | 6014966 | * | 1/1994 | 604/385.1 |

* cited by examiner

*Primary Examiner*—Dennis Ruhl
*Assistant Examiner*—K. M. Reichle
(74) *Attorney, Agent, or Firm*—Lowe Hauptman Gilman & Berner, LLP

(57) ABSTRACT

A disposable diaper includes a topsheet, a backsheet and an absorbent core therebetween. The topsheet is composed of a central sheet covering the core and a pair of side sheets lying at transversely opposite sides of the central sheet and extending longitudinally of the diaper, together with the backsheet. Each side sheet has a proximal zone bonded to the backsheet without overlapping a side edge of the central sheet bonded to the backsheet. An outer zone bonded to the remaining zone of the backsheet lying outside the proximal zone forms an elasticized first side flap and an inner zone extending above the central zone forms an elasticized second side flap.

5 Claims, 2 Drawing Sheets

DISPOSABLE DIAPER

This application is a continuation of application Ser. No. 08/632,828 filed Apr. 16, 1996, now abandoned.

BACKGROUND OF THE INVENTION

The present invention relates to a disposable diaper for absorption and containment of body fluids.

Conventional disposable diapers generally comprise a liquid-permeable topsheet made of nonwoven fabric, a liquid-impermeable backsheet made of plastic film and a liquid-absorbent core disposed between these sheets. The topsheet and the backsheet are bonded to each other at portions thereof extending outwardly beyond transversely and longitudinally opposite edges of the core so as to form leg-surrounding flaps and a waist-surrounding flap, respectively. In such diapers, a pair of hydrophobic nonwoven fabrics are attached to an upper surface of the topsheet at the leg-surrounding flaps and elastic members are secured to these nonwoven fabrics along the inner free edges of the leg-surrounding flaps so that these inner free edges may rise on an inner surface of the diaper in order to avoid sideway leakage of body fluids possibly occurring around the legs of a wearer.

With such diapers, body fluids discharged onto the topsheet are absorbed through the topsheet into the core and at the same time laterally spread through the topsheet into the leg-surrounding flaps, possibly causing sideway leakage and giving a wearer an uncomfortable wet feeling. While such sideway leakage, as well as wet feeling, can be alleviated by attaching the hydrophobic nonwoven fabrics to an inner surface of the respective flaps, the amount of body fluids having spread into the hydrophilic topsheet underlying the hydrophobic nonwoven fabric soon exudes on the surfaces of the respective hydrophobic nonwoven fabrics and possibly increases the wet feeling.

Therefore, it is an object of the present invention to provide a disposable diaper having a pair of side flaps which improve the effect of preventing sideway leakage of body fluids.

SUMMARY OF THE INVENTION

According to the present invention, there is provided a disposable diaper comprising a topsheet, a backsheet and an absorbent core disposed therebetween. The topsheet comprises a central sheet covering the core and a pair of side sheets lying at transversely opposite sides of the central sheet and extending longitudinally of the diaper together with the backsheet. The central sheet has transversely opposite side edges and longitudinally opposite end edges extending outwardly from a periphery of the core, the side and end edges being bonded to the backsheet. Each side sheet has a proximal zone, an inner zone extending inwardly from the proximal zone and having a distal edge opposed to the proximal zone, and an outer zone extending outwardly from the proximal zone. The proximal zone is bonded to the backsheet without an overlapping side edge of the central zone but in side-by-side relationship with the side edge. The outer zone is bonded to the remaining zone of the backsheet lying outside the proximal zone to form a first side flap. The inner zone extends above the central sheet to form a second side flap and is bonded at longitudinally opposite ends of the inner zone to the central sheet. The first side flap is provided adjacent an outer side edge thereof with an elastic member in an elastically contractible condition. The second side flap is provided along the distal edge of the inner zone with an elastic member in an elastically contractible condition.

The inventive diaper, as described hereinabove, allows a side edge of the central sheet and the proximal portion of the side sheet to be brought into contact with or separated from each other without overlapping each other. In consequence, body fluids are effectively prevented by the side edge of the central sheet from further spreading, i.e., the body fluids cannot spread beyond the proximal zone of the side sheet to the leg-surrounding flap.

Even if the side edge of the central sheet and the proximal zone of the side sheet are separated from each other, as mentioned above, and the location of the applied adhesive is exposed between the side edge of the central zone and the proximal portion, i.e., the inner zone of the side sheet, the second side flap extending above the exposed zone prevents said exposed zone from contacting a wearer's skin.

Furthermore, where the side edge of the central sheet and the proximal portion of the side sheet are separated from each other, the first side flap curves or stands up more easily along the separated zone defined between the side edge and the proximal zone under the contractible force of the elastic member associated with the first side flap, because the separated zone is more flexible than the remaining zone of the first side flap. Accordingly, the first side flap provides a close contact with a wearer's skin along the associated zone thereof with the elastic member.

DETAILED DESCRIPTION OF THE PREFERRED EMBODIMENT

Figure 1:
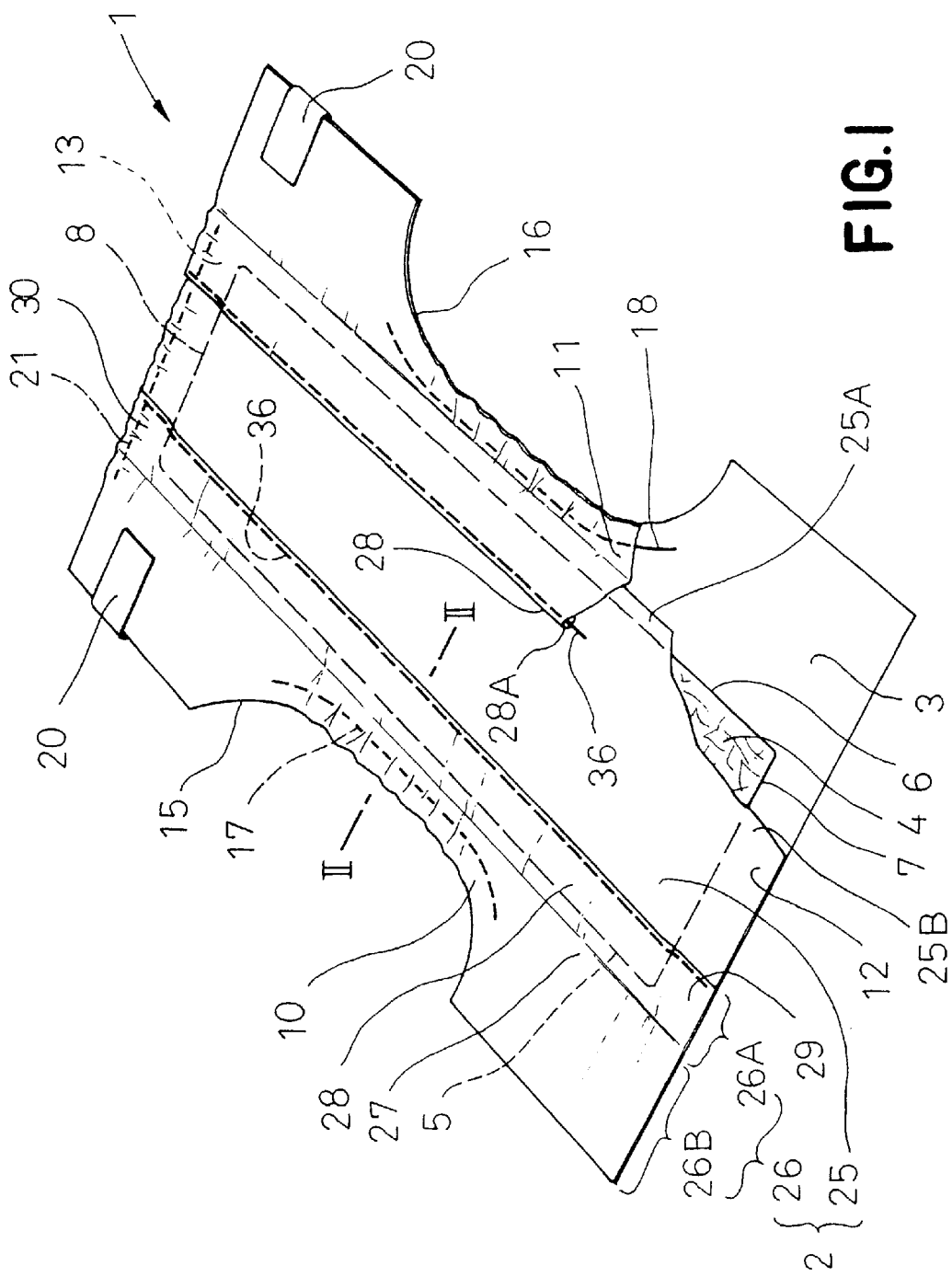
FIG. 1 is a perspective view showing a disposable diaper as partially broken away.

Referring to FIG. 1, a diaper 1 comprises a topsheet 2, a backsheet 3 and a substantially rectangular liquid-absorbent core 4 disposed between these sheets 2, 3. The topsheet 2 and backsheet 3 extend outwardly beyond transversely opposite edges 5, 6 and longitudinally opposite edges 7, 8 of the core 4 and are bonded to each other at these outer extensions so as to form transversely opposite first side flaps 10, 11 and longitudinally opposite end flaps 12, 13, respectively. The first side flaps 10, 11 are provided with cutouts 15, 16 curved to define respective leg-holes and elastic members 17, 18 for the respective leg-holes are bonded in an elastically contractible condition to at least one of the topsheet 2 and backsheet 3 on inner surface(s) thereof along and inside edges of the respective cutouts 15, 16, respectively. Conventional tape fasteners 20 are attached to the side flaps 10, 11 adjacent rear ends thereof. Elastic member 21 for the waist-hole is secured in an elastically contractible condition to at least one of the topsheet 2 and backsheet 3 on inner surface(s) thereof along and inside an edge of the end flap 13.

The topsheet 2 comprises a central sheet 25 and a pair of side sheets 26 separately provided on either side of the central sheet 25. The central sheet 25 is liquid-permeable and extends outwardly beyond a periphery of the core 4 to define transversely opposite side edges 25A and longitudinally opposite end edges 25B, these edges 25A, 25B being bonded to the backsheet 3. Each of the side sheets 26 is liquid-permeable or liquid-impermeable and comprises a proximal zone 27 extending longitudinally of the diaper 1 and bonded to the backsheet 3, an inner zone 26A extending inwardly from the proximal zone 27 and having a distal edge 28 lying above the central sheet 25 and an outer zone 26B extending outwardly from the proximal zone 27 and bonded to the backsheet 3. Longitudinally opposite ends 29, 30 of the inner zone 26A are bonded to the central sheet 25 and the distal edge 28 is folded in two to form a sleeve portion 28A so that an elastic member 36 may be secured in an elastically contractible condition between the longitudinally opposite ends 29, 30 to the inner surface of the sleeve Portion 28A. Thus, the inner zone 26A forms a second side flap serving as a leakage barrier.

The backsheet 3 is liquid-impermeable and has the same shape as that of the diaper 1.

Figure 2:
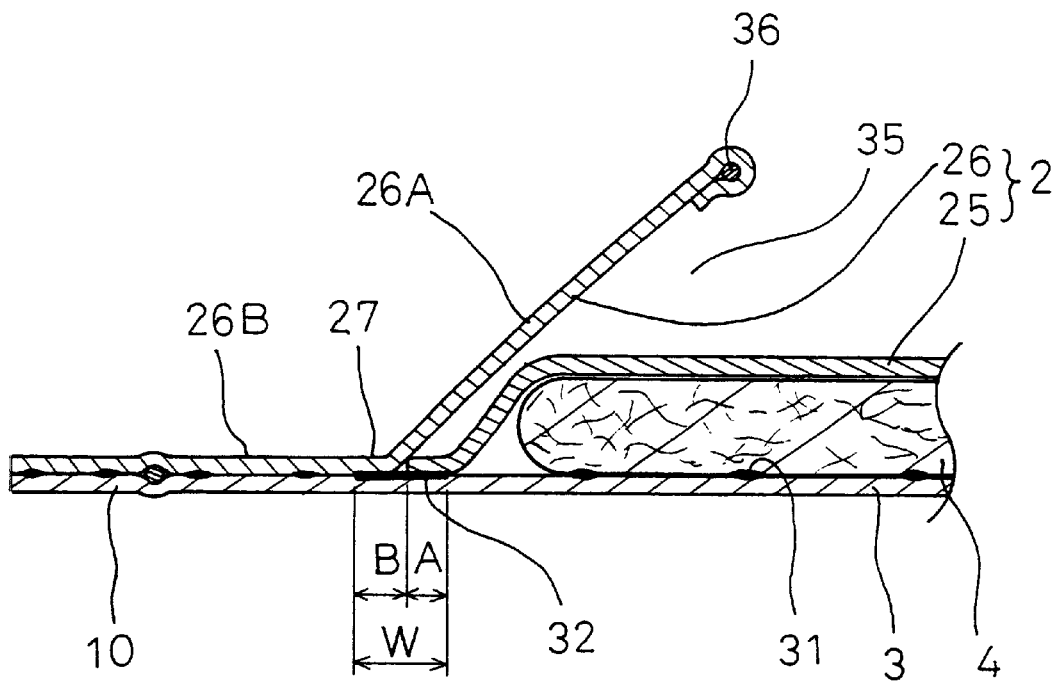
FIG. 2 is a sectional view taken along a line II—II in FIG. 1.

With reference to FIG. 2, an adhesive means 31, such as hot melt adhesive, is applied to an upper surface of the backsheet 3 at selected locations thereon; thereby the topsheet 2 and the core 4 are bonded to the backsheet 3. In particular, one of the adhesive applied locations 32 lies outside the associated side edge 5 or 6 of the core 4 and extends between longitudinally opposite ends of the diaper with a width W=A+B. The side edge 25A of the central sheet 25 is bonded to the backsheet 3 over the width A and the proximal zone 27 of the side sheet 26 is bonded to the backsheet 3 over the width B extending outside the width A. The inner zone 26A of the side sheet 26 tends to rise obliquely on the proximal zone 27 and to form together with the central sheet 25 a pocket 35 opening toward the center of the diaper 1. It should be understood, however, that the inner zone 26A will loosely overlap the central sheet 25 with the pocket 35 being substantially closed so far as the diaper 1 is longitudinally developed as shown in FIG. 1. The elastic member 36 will contract, causing the inner zone 26A to rise and to open the pocket 35 as shown by FIG. 2 only when the diaper 1 is worn to be curved according to the curve of a wearer's body.

With the diaper 1 constructed as described hereinabove, most of body fluids are absorbed through the central sheet 25 into the core 4 and the rest possibly flows sideways but is reliably received by the pockets 35 without any apprehension of sideway leakage. Even when an amount of body fluids spreads over the central sheet 25, further spread is prevented by the side sheets 26 when they are liquid-impermeable and serve as reliable barriers. Thereby the side flaps 10 are maintained in dry conditions. To improve such spread-barrier effect, the proximal zones 27 of the side sheets 26 are preferably located adjacent the respective side edges of the central sheet 25. More preferably, the adhesive applied locations having the widths A and B. respectively, are more or less separated from each other as shown.

To bond the central sheet 25 and the side sheet 26 to the backsheet 3, an adhesive means, such as hot melt adhesive, is applied to the backsheet 3 to form the adhesive applied location 32 and the central sheet 25 is bonded to a part of the adhesive applied location 32. Then, the inner zone 26A of the side sheet 26 is placed on an upper surface of the central sheet 25 and a portion of the side sheet adapted to form the proximal zone 27 is bonded to the remaining part of the adhesive applied location 32 without overlapping the already bonded portions of the central sheet 25, but in side-by-side relationship with the central sheet 25, i.e., transversely opposed to the central sheet 25. At the same time, the outer zone 26B of the side sheet 26 is bonded to an upper surface of the backsheet 3. Transversely opposed edges of these bonded portions of the central sheet 25 and the respective side sheets 26 may be in contact with each other or separated from each other. When it is desired to separate them from each other, they are separated from each other preferably by less than 5 mm.

According to the invention, a hydrophilic or hydrophobic nonwoven fabric is used for the central sheet 25 and a nonwoven fabric or plastic film having a hydrophobicity higher than that of the central sheet 25 is used for the side sheets 26. In other words, the central sheet 25 is formed of a nonwoven fabric having a hydrophobicity higher than that of the side sheets 26. A sheet having a hydrophobicity similar to or higher than that of the side sheets 26 may be used for the backsheet 3. The other components of the diaper may be formed of respective materials conventionally used in the related industrial field. For bonding of the various components, Ax not only an adhesive means, such as hot melt adhesive, but also heating means may be used.

What is claimed is:

1. A disposable diaper having a longitudinal axis, comprising:

a topsheet;

a backsheet;

an absorbent core disposed between said topsheet and said backsheet which respectively extend outwardly from longitudinally opposite end edges and transversely opposite side edges of said core;

said topsheet comprising a central sheet and a pair of side sheets, said central and side sheets extending along said longitudinal axis together with said backsheet;

said central sheet lying on an upper surface of said core, said central sheet being bonded at longitudinally opposite end edges and transversely opposite side edges thereof to said backsheet;

each of said side sheets lying on a respective one of a pair of side zones of said backsheet defined between transverse side edges of said backsheet and associated ones of the transversely opposite side edges of said central sheet, each of said side sheets having a proximal zone, an inner zone inward from said proximal zone, a distal edge opposed to said proximal zone and an outer zone extending outwardly from said proximal zone, each proximal zone being bonded to said respective one of the pair of side zones of said backsheet without overlying the associated one of the transversely opposite side edges of said central sheet but in side-by-side relationship with the associated one of the transversely opposite side edges of said central sheet, each outer zone being bonded to the said respective one of the pair of side zones of said backsheet to form a first side flap, each inner zone extending above said central sheet to form a second side flap and being bonded at longitudinally opposite ends of said inner zone to said central sheet; and said first and second side flaps being provided with an elastic member in an elastically contractible condition;

wherein the associated one of the transversely opposite side edges of said central sheet and each proximal zone are bonded in said side-by-side relationship to an adhesive zone applied longitudinally of said backsheet, wherein said adhesive zone is in the form of a transversely extending single band of adhesive to which both the associated one of the transversely opposite side edges of said central sheet and each proximal zone are bonded in said side-by-side relationship.

2. A disposable diaper according to claim 1, wherein said central sheet is made of a relatively hydrophilic nonwoven fabric and said side sheets are formed of a relatively hydrophobic nonwoven fabric.

3. A disposable diaper according to claim 1, wherein said backsheet is formed of a sheet having a hydrophobicity similar to or higher than said side sheets.

4. A disposable diaper according to claim 1, wherein the associated one of the transversely opposite side edges of said central sheet and each proximal zone are separated from each other by less than 5 mm.

5. A disposable diaper according to claim 1, wherein each proximal zone is bonded along an entire length thereof to the respective one of the pair of side zones of said backsheet.

\* \* \* \* \*